(12) United States Patent
Burney

(10) Patent No.: US 8,580,770 B2
(45) Date of Patent: Nov. 12, 2013

(54) METHOD OF TREATING ACTINIC KERATOSIS AND BASAL CELL CARCINOMA

(76) Inventor: Bryan Burney, McCordsville, IN (US)

(*) Notice: Subject to any disclaimer, the term of this patent is extended or adjusted under 35 U.S.C. 154(b) by 30 days.

(21) Appl. No.: 13/479,647

(22) Filed: May 24, 2012

(65) Prior Publication Data

US 2012/0302529 A1 Nov. 29, 2012

Related U.S. Application Data

(60) Provisional application No. 61/490,456, filed on May 26, 2011.

(51) Int. Cl.
*A61K 31/618* (2006.01)

(52) U.S. Cl.
USPC .......................................... 514/163

(58) Field of Classification Search
USPC .......................................... 514/163
See application file for complete search history.

(56) References Cited

U.S. PATENT DOCUMENTS

| 6,403,565 | B1 * | 6/2002 | von Borstel et al. | 514/45 |
| 8,080,237 | B2 * | 12/2011 | Sredni et al. | 424/59 |
| 8,110,582 | B2 * | 2/2012 | Egging et al. | 514/279 |

* cited by examiner

*Primary Examiner* — Raymond Henley, III
(74) *Attorney, Agent, or Firm* — Woodard, Emhardt, Moriarty, McNett & Henry LLP

(57) ABSTRACT

A method for treating actinic keratosis or basal cell carcinoma. A person's skin is inspected to identify areas that exhibit lesions indicating actinic keratosis or basel cell carcinoma. If such areas are found, a treating composition is applied to the skin in that area. The treating composition may include avobenzone, octocrylene, octyl salicylate, and oxybenzone, and optionally may additionally include SD alcohol 40, $C_{12-15}$ alkyl benzoate, acrylates, octylacrylamide copolymer, hydroxypropyl cellulose, PEG-40 sorbitan peroleate, tocopherol, and aloe barbadensis extract. The skin is monitored regularly to determine whether the skin lesions remain, and the treating composition is applied several times daily for a period of at least two months until the area is substantially free of the lesions.

20 Claims, No Drawings

METHOD OF TREATING ACTINIC KERATOSIS AND BASAL CELL CARCINOMA

REFERENCE TO RELATED APPLICATIONS

This application claims the benefit of U.S. Provisional Patent Application Ser. No. 61/490,456, filed May 26, 2011, which is hereby incorporated herein by reference.

BACKGROUND OF THE INVENTION

Actinic keratosis is a pre-cancerous form of hyperkaratosis that is known to be caused by frequent or extreme exposure of the skin to sunlight. The condition typically presents as small, rough patches of skin approximately 2 mm to 7 mm in diameter. The patches are usually reddish in color, with rough texture and whitish or yellow scales. Actinic keratosis is frequently painful, and may develop to a malignant condition without treatment and upon continued exposure to the sun.

Actinic keratosis is most commonly treated topically, with creams such as photodynamic creams, imiquimod, diclofenac, Ag3derm or 5-fluorouracil. Alternatively, the condition may be treated by cryosurgery with liquid nitrogen. When these methods fail, the keratosis may be excised surgically, or treated by laser therapy.

Basal cell carcinoma is the most common form of skin cancer and accounts for more than 90% of all skin cancer in the U.S. These cancers almost never spread (metastasize) to other parts of the body, although they can cause damage by growing and invading surrounding tissue.

Basal cell carcinomas usually present initially as a small, dome-shaped bump. The bump may be covered by small, superficial blood vessels that cause the spot to appear shiny and translucent, sometimes looking "pearly." Some basal cell carcinomas contain melanin pigment, making them look dark rather than shiny.

Basal cell carcinoma may be treated by curettage and desiccation, which typically involves scooping out the basal cell carcinoma with a spoon like curette. Desiccation is the additional application of an electric current to control bleeding and kill the remaining cancer cells.

Other treatments for basal cell carcinoma include surgical excision and radiation therapy. Cryosurgery may be used, typically using liquid nitrogen to freeze and kill the abnormal cells.

None of the prior art treatments for actinic keratosis and/or basal cell carcinoma has proven to be effective for all patients, and some are extremely expensive and/or highly invasive. A need therefore exists for improved compositions and method for treating actinic keratosis and/or basal cell carcinoma. The present invention addresses that need.

SUMMARY OF THE INVENTION

Briefly describing one aspect of the present invention, there is provided a method for treating actinic keratosis or basal cell carcinoma. A person's skin is inspected to identify areas that exhibit lesions indicating actinic keratosis or basel cell carcinoma. If such areas are found, a treating composition is applied to the skin in that area. The treating composition preferably includes avobenzone, octocrylene, octyl salicylate, and oxybenzone, and optionally may additionally include SD alcohol 40, $C_{12-15}$ alkyl benzoate, acrylates, octylacrylamide copolymer, hydroxypropyl cellulose, PEG-40 sorbitan peroleate, tocopherol, and aloe barbadensis extract. The skin is monitored regularly to determine whether the skin lesions remain, and the treating composition is applied several times daily for a period of at least two months until the area is substantially free of the lesions.

DESCRIPTION OF THE PREFERRED EMBODIMENTS

For the purposes of promoting an understanding of the principles of the invention, reference will now be made to certain preferred embodiments and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

As indicated above, one aspect of the present invention relates to a method for treating actinic keratosis. One step in the method may be to identify an area of a person's skin that exhibits lesions indicating actinic keratosis. Another step in the method may be to apply to that area a treating composition comprising avobenzone, octocrylene, octyl salicylate, and oxybenzone. A third step in the method may be to monitor the skin area regularly to determine whether the skin lesions remain. A fourth step in the method is to repeat said applying step several times daily for a period of at least two months until the area is substantially free of the lesions.

In one embodiment the treating composition comprises avobenzone, octocrylene, octyl salicylate, oxybenzone, and one or more compositions selected from the group consisting of SD alcohol 40, $C_{12-15}$ alkyl benzoate, acrylates, octylacrylamide copolymer, hydroxypropyl cellulose, PEG-40 Sorbitan Peroleate, Tocopherol, and aloe barbadensis extract. The applying step may be performed twice daily for a period of at least three months until the area is substantially free of the lesions. In one embodiment the applying step is repeated twice daily for a period of up to six months.

In another embodiment of the present invention the treating compositions may be used to treat basal cell carcinoma. One step in that method is to identify an area of a person's skin that exhibits lesions indicating basal cell carcinoma. If such areas are found a treating composition is applied to the area, with the treating composition preferably including avobenzone, octocrylene, octyl salicylate, and oxybenzone. As in the method of treating actinic keratosis, the third step in the method is to monitor the skin area regularly to determine whether the skin lesions remain. A fourth step in the method is to repeat said applying step several times daily for a period of at least two months until the area is substantially free of the lesions.

The treating compositions used to treat basal cell carcinoma may comprise avobenzone, octocrylene, octyl salicylate, oxybenzone, and one or more compositions selected from the group consisting of SD alcohol 40, $C_{12-15}$ alkyl benzoate, acrylates, octylacrylamide copolymer, hydroxypropyl cellulose, PEG-40 sorbitan peroleate, tocopherol, and aloe barbadensis extract. In one embodiment the treating composition is the composition that was sold from about 2006 through about 2010 under the trade name Coppertone Sport Gel (SPF 30). The active ingredients were indicated to be: Avobenzone (PARSOL 1789), Octocrylene, Octyl Salicylate, and Oxybenzone; and the inactive ingredients were indicated to be: SD Alcohol 40 (78.7% V/V), C12-15 Alkyl Benzoate, Acrylates/Octylacrylamide copolymer, Hydropropylcellulose, PEG-40, Sorbitan Peroleate, Tocopheral (VITAMIN E), Aloe Barbadensis Extract, and Fragrance.

As with the method for treating actinic keratosis, basal cell carcinoma may be treated by applying the treating composition about twice daily for a period of at least three months until the area is substantially free of the lesions. The applying step may be repeated twice daily for a period of up to six months.

Further describing certain aspects and/or terms used in this specification and/or claims, the step of identifying an area of a person's skin that exhibits lesions indicating actinic keratosis or basal cell carcinoma may be accomplished by visually inspecting the skin to see whether there are any patches of skin that indicate one of those conditions. For actinic keratosis, the condition typically presents as a rough patch of skin, approximately 2 mm to 7 mm in diameter, that is reddish or pink in color, and which may have whitish or yellow scales. For basal cell carcinoma, the condition may present as a shiny, pearly nodule, or as a red patch like eczema. In some cases, infiltrative or morpheaform basal-cell cancers can present as a skin thickening or scar tissue.

The inspection may be performed by trained medical personnel, or by any person who has been instructed in identifying skin conditions indicating actinic keratosis and/or basal cell carcinoma.

Once a potential actinic keratosis site or a potential basal cell carcinoma site has been identified, the next step is to apply to that area a treating composition comprising avobenzone, octocrylene, octyl salicylate, and oxybenzone. The applying step may be accomplished by rubbing a small amount of the treating composition into the skin, as is commonly done when applying topical creams and/or ointments. Alternatively, the treating composition may be dabbed on without rubbing, or by other methods that provide better coverage on areas such as protruding papules.

After the treating composition has been applied to the skin, the skin is monitored to determine whether the skin lesions remain. The monitoring is preferably done regularly, which for the purposes of this disclosure is at least several times a week and preferably about daily. As with the initial inspection to identify areas of a person's skin that exhibit lesions indicating actinic keratosis or basal cell carcinoma, the monitoring step may be accomplished by visually inspecting the skin to see whether there are any patches of skin that indicate one of those conditions. The inspection may be performed by the patient if the patient is capable of recognizing whether the skin continues to exhibit an appearance indicating actinic keratosis or basal cell carcinoma.

A fourth step in the method is to repeat said applying step several times daily for a period of at least two months until the area is substantially free of the lesions. This aspect of the invention does not require applying the treating composition every day without missing any days, or require applying the treating composition twice a day without missing any treatments. It is understood that the treatments should occur "regularly," which may be daily or nearly every day, with treatments being done about twice a day on most days. It is understood that a patient may miss an occasional treatment, and may even miss an occasional day. Further, some patients may tolerate more that two applications daily while others may tolerate only one or two treatments daily. The treating composition should be applied frequently enough to provide effective treatment while avoiding inflammation of the skin and/or salicylic acids burns.

In some embodiments the treating composition is applied to the skin once or twice a day for a period of between two months and six months while monitoring the size of the skin lesions. Treatment ends when the skin lesions are gone.

The treating compositions may include one or more salicylate compounds which are effective to function as a cox 1 blocker when applied to the skin. Preferred amounts of the salicylate compound(s) may be in the range of about 0.5% and about 20%.

The treating compositions preferably include avobenzone, which may function as a sunscreen and/or as an ultraviolet (UVA) light absorber). The amount of avobenzone may vary between about 0.5% and about 20%.

The treating compositions preferably include octocrylene, which may function as a sunscreen and/or as an ultraviolet light absorber. The amount of octocrylene may vary between about 0.5% and about 20%.

The treating compositions preferably include octyl salicylate, which may function as a sunscreen and/or as an ultraviolet (UVB) light absorber. The amount of octyl salicylate may vary between about 0.5% and about 20%.

The treating compositions preferably include oxybenzone, which may function as a sunscreen and/or as an ultraviolet light absorber. The amount of oxybenzone may vary between about 0.5% and about 20%.

The treating compositions may include SD alcohol 40 (78.7% V/V), which may function as an astringent, a solvent, and/or a viscosity decreasing agent. The amount of SD alcohol 40 may vary between about 0.05% and about 20%.

The treating compositions may include $C_{12\text{-}15}$ alkyl benzoate, which may function as a skin conditioner and/or emollient. The amount of $C_{12\text{-}15}$ alkyl benzoate may vary between about 0.05% and about 10%.

The treating compositions may include one or more acrylates. The amount of the acrylates may vary between about 0.05% and about 10%.

The treating compositions may include octylacrylamide copolymer, which may function as a sunscreen and/or as an ultraviolet light absorber. The amount of octylacrylamide copolymer may vary between about 0.05% and about 10%.

The treating compositions may include hydroxypropyl cellulose, which may function as a sunscreen and/or as an ultraviolet light absorber. The amount of hydroxypropyl cellulose may vary between about 0.05% and about 5%.

The treating compositions preferably include PEG-40 sorbitan peroleate, which may function as an emulsifying agent and/or as a solubilizing agent. The amount of $C_{12\text{-}15}$ alkyl benzoate may vary between about 0.05% and about 5%.

The treating compositions may include tocopherol (vitamin E). The amount of tocopherol is preferably between about 0.05% and about 5%.

The treating compositions may include aloe barbadensis extract, which may function as a external analgesic and/or a humectant and/or a skin-conditioning emollient. The amount of aloe barbadensis extract is preferably between about 0.05% and about 5%.

In addition to the above, other excipients, stabilizers, fillers, solvents, surfactants, etc. may be included in the treating composition. When included, such additional components are preferably present in amounts between about 0.01% and about 20% of the composition.

Reference will now be made to specific examples using the processes described above. It is to be understood that the examples are provided to more completely describe preferred embodiments, and that no limitation to the scope of the invention is intended thereby.

Example 1

A male was examined and found to have a clinically obvious basal cell cancer in his right cheek. Excision of the cancer was recommended. Instead, the patient was treated by applying a treating composition to the cancer. The treating composition comprised avobenzone, octocrylene, octyl salicylate, oxybenzone, SD alcohol 40, $C_{12-15}$ alkyl benzoate, acrylates, octylacrylamide copolymer, hydroxypropyl cellulose, PEG-40 sorbitan peroleate, tocopherol, and aloe barbadensis extract. The skin was monitored and the treating composition was re-applied twice daily for a period of approximately six months until the area was substantially free of the lesions. The area remained free of the cancer following the treatment.

Example 2

A male was examined and found to have a clinically obvious basal cell cancer in his cheek and forehead. The patient was treated by applying a treating composition to both areas. The treating composition comprised avobenzone, octocrylene, octyl salicylate, oxybenzone, SD alcohol 40, $C_{12-15}$ alkyl benzoate, acrylates, octylacrylamide copolymer, hydroxypropyl cellulose, PEG-40 sorbitan peroleate, tocopherol, and aloe barbadensis extract. The skin was monitored and the treating composition applied twice daily for a period of approximately three months until the area was substantially free of the lesions. The area remained free of the cancer following the treatment.

Example 3

A 62 year old white female with a long history of sun exposure and multiple childhood sunburns developed recurrent basal cell carcinoma in the deep fold of her right nasal ala. She had a Mohs procedure at the same site four years previously. The recurrent basal cell carcinoma consisted of two papules, approximately 2 mm and 1 mm in diameter respectively. Plastic surgery and Radiation Oncology consults confirmed clinically obvious recurrent basal cell carcinoma.

Treatment with the composition comprising avobenzone, octocrylene, octyl salicylate, oxybenzone, SD alcohol 40, $C_{12-15}$ alkyl benzoate, acrylates, octylacrylamide copolymer, hydroxypropyl cellulose, PEG-40 sorbitan peroleate, tocopherol, and aloe barbadensis extract was initiated. The composition was provided as a gel that is applied in as thick a layer as possible to the affected skin over an approximate 2 centimeter diameter area twice daily. Mild reduction in inflammation was noted on video microscope images (40× magnification) after one week.

Example 4

A patient develops two papules of basal cell carcinoma and is treated with a gel composition sold during the summer of 2011 under the tradename Coppertone Sport Sunblock gel. The larger carcinoma initially measures about 2.5 mm in diameter, and is located on the nasal ala. The smaller carcinoma initially measures about 2 mm, and is adjacent to and redder than the larger carcinoma.

The two carcinomas are treated by applying the gel to the skin over and around the papules twice daily. The gel composition comprises avobenzone, octocrylene, octyl salicylate, oxybenzone, SD alcohol 40, $C_{12-15}$ alkyl benzoate, acrylates, octylacrylamide copolymer, hydroxypropyl cellulose, PEG-40 sorbitan peroleate, tocopherol, and aloe barbadensis extract.

Reduction in inflammation is noted after several weeks, and within three months the smaller carcinoma is substantially resolved. The larger carcinoma is somewhat smaller, and some new hair growth at the margins of the area is noted.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

The invention claimed is:

1. A method for treating actinic keratosis, comprising identifying an area of a person's skin that exhibits lesions indicating actinic keratosis; applying to that area a treating composition comprising avobenzone, octocrylene, octyl salicylate, and oxybenzone; monitoring the skin area regularly to determine whether the skin lesions remain; and repeating said applying step at least twice daily for a period of at least two months until the area is substantially free of the lesions.

2. A method according to claim 1 wherein said treating composition further includes SD alcohol 40.

3. A method according to claim 1 wherein said treating composition further includes $C_{12-15}$ alkyl benzoate.

4. A method according to claim 1 wherein said treating composition further includes acrylates.

5. A method according to claim 1 wherein said treating composition further includes octylacrylamide copolymer.

6. A method according to claim 1 wherein said treating composition further includes hydroxypropyl cellulose.

7. A method according to claim 1 wherein said treating composition further includes PEG-40 Sorbitan Peroleate.

8. A method according to claim 1 wherein said treating composition further includes Tocopherol.

9. A method according to claim 1 wherein said treating composition further includes aloe barbadensis extract.

10. A method for treating actinic keratosis, comprising identifying an area of a person's skin that exhibits lesions indicating actinic keratosis; applying to that area a treating composition comprising avobenzone, octocrylene, octyl salicylate, oxybenzone, SD alcohol 40, $C_{12-15}$ alkyl benzoate, acrylates, octylacrylamide copolymer, hydroxypropyl cellulose, PEG-40 Sorbitan Peroleate, Tocopherol, and aloe barbadensis extract; monitoring the skin area daily to determine whether the skin lesions remain, and repeating said applying step several times daily for a period of at least two months until the area is substantially free of the lesions.

11. A method for treating basal cell carcinoma, comprising identifying an area of a person's skin that exhibits lesions indicating basal cell carcinoma; applying to that area a treating composition comprising avobenzone, octocrylene, octyl salicylate, and oxybenzone; monitoring the skin area regularly to determine whether the skin lesions remain; and repeating said applying step several times daily for a period of at least two months until the area is substantially free of the lesions.

12. A method according to claim 11 wherein said treating composition further includes SD alcohol 40.

13. A method according to claim 11 wherein said treating composition further includes $C_{12-15}$ alkyl benzoate.

14. A method according to claim 11 wherein said treating composition further includes acrylates.

15. A method according to claim 11 wherein said treating composition further includes octylacrylamide copolymer.

16. A method according to claim 11 wherein said treating composition further includes hydroxypropyl cellulose.

17. A method according to claim 11 wherein said treating composition further includes PEG-40 Sorbitan Peroleate.

18. A method according to claim 11 wherein said treating composition further includes Tocopherol.

19. A method according to claim 11 wherein said treating composition further includes aloe barbadensis extract.

20. A method for treating basal cell carcinoma, comprising identifying an area of a person's skin that exhibits lesions indicating basal cell carcinoma; applying to that area a treating composition comprising avobenzone, octocrylene, octyl salicylate, oxybenzone, SD alcohol 40, $C_{12-15}$ alkyl benzoate, acrylates, octylacrylamide copolymer, hydroxypropyl cellulose, PEG-40 sorbitan peroleate, tocopherol, and aloe barbadensis extract; monitoring the skin area daily to determine whether the skin lesions remain, and repeating said applying step several times daily for a period of at least two months until the area is substantially free of the lesions.

\* \* \* \* \*